(12) United States Patent
Matsukawa et al.

(10) Patent No.: US 8,134,033 B2
(45) Date of Patent: Mar. 13, 2012

(54) FLUOROCOMPOUND HAVING HIGHLY FLUORINATED NORBORNANE STRUCTURE, FLUOROPOLYMER, AND THEIR PRODUCTION PROCESSES

(75) Inventors: Yasuhisa Matsukawa, Chiyoda-ku (JP); Daisuke Shirakawa, Chiyoda-ku (JP); Eisuke Murotani, Chiyoda-ku (JP); Naoko Shirota, Chiyoda-ku (JP); Yoko Takebe, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 583 days.

(21) Appl. No.: 12/351,905

(22) Filed: Jan. 12, 2009

(65) Prior Publication Data

US 2009/0192330 A1 Jul. 30, 2009

Related U.S. Application Data

(63) Continuation of application No. PCT/JP2007/063401, filed on Jul. 4, 2007.

(30) Foreign Application Priority Data

Jul. 11, 2006 (JP) .................................. 2006-190484

(51) Int. Cl.
C07C 49/467 (2006.01)
C07C 67/14 (2006.01)
C07C 69/653 (2006.01)
C08F 20/22 (2006.01)

(52) U.S. Cl. ......... 568/817; 568/816; 560/219; 560/220

(58) Field of Classification Search .................. None
See application file for complete search history.

(56) References Cited

U.S. PATENT DOCUMENTS

2005/0130056 A1* 6/2005 Ogata et al. ................ 430/270.1

FOREIGN PATENT DOCUMENTS

| EP | 2 009 499 A1 | 12/2008 |
|---|---|---|
| JP | 2002-80431 | 3/2002 |
| JP | 2002-327013 | 11/2002 |
| JP | 2005-133065 | 5/2005 |
| JP | 2005-272741 | 10/2005 |
| WO | WO 2007/066481 A1 | 6/2007 |
| WO | WO 2007/119803 A1 | 10/2007 |
| WO | WO 2007/145288 A1 | 12/2007 |

* cited by examiner

OTHER PUBLICATIONS

U.S. Appl. No. 12/254,030, filed Oct. 20, 2008, Takebe, et al.

*Primary Examiner* — Daniel Sullivan
*Assistant Examiner* — Yevegeny Valenrod
(74) *Attorney, Agent, or Firm* — Oblon, Spivak, McClelland, Maier & Neustadt, L.L.P.

(57) ABSTRACT

To provide a novel polymerizable fluorocompound having a highly fluorinated norbornane structure, and a polymer obtained from the compound. Further, their production processes and a novel intermediate useful for the processes.

A novel compound (1) such as a compound (11) or a compound (12), and its polymer. A compound (2) such as a compound (21) or (22), and a compound (3) such as a compound (31) or (32$^M$), which are useful as an intermediate for the production of the compound (1), and its production process. However, each of $Z^A$ to $Z^E$ represents such as —CH(—OC(O)C(CH$_3$)=CH$_2$)— or —CF$_2$—, Each of $W^A$ and $W^B$ represents such as F, each of $Y^A$ to $Y^E$ represents such as —CH(—OH)— or —CF(CH$_2$OH), and each of $X^A$ to $X^E$ represents such as —C(O)— or —CF$_2$—.

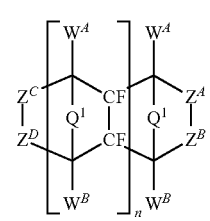

(1)

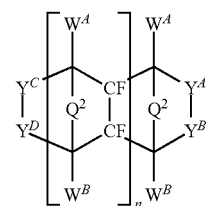

(2)

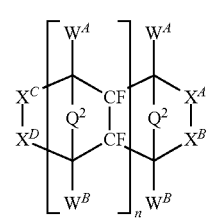

(3)

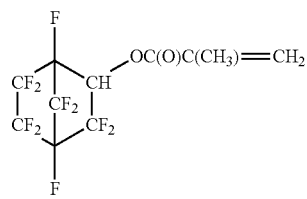

(11)

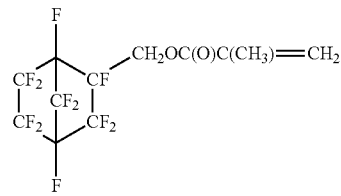

(12)

-continued
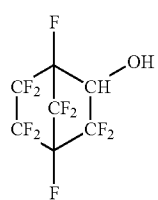
(21)
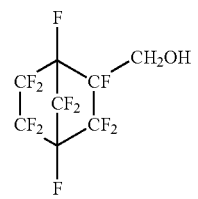
(22)
-continued
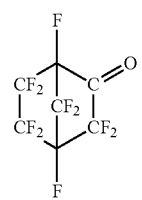
(31)
(32^M)
8 Claims, No Drawings

FLUOROCOMPOUND HAVING HIGHLY FLUORINATED NORBORNANE STRUCTURE, FLUOROPOLYMER, AND THEIR PRODUCTION PROCESSES

TECHNICAL FIELD

The present invention relates to a novel compound having a highly fluorinated norbornane structure, a fluoropolymer obtained from the compound, and their production processes.

BACKGROUND ART

A polymerizable fluorocompound is useful as a monomer for producing a fluoropolymer excellent in physical properties such as transparency, water and oil repellency, heat resistance, mold releasability or chemical resistance. For example, a (meth)acrylate (in the present specification, a (meth)acrylate is a collective term of an acrylate and a methacrylate) having a polyfluoroalkyl group is useful as a monomer for producing a fluoropolymer to be used as an antifouling agent, a water and oil repellent, a mold lubricant, etc.

In order to improve the physical properties of the above fluoropolymer, various polymerizable fluorocompounds are reported. For example, the following compound wherein an acyclic perfluoroalkyl group portion and a $CH_2$=CClC(O)O—portion are connected via a norbornane structure, is reported (cf. Patent Document 1):

Patent Document 1: JP-A-2005-272741

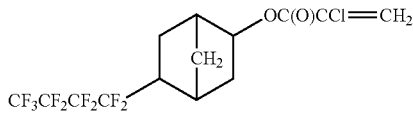

DISCLOSURE OF THE INVENTION

Object to be Accomplished by the Invention

However, a polymerizable fluorocompound having a highly fluorinated norbornane structure and its production process have been unknown. Further, a polymer obtained from such a fluorocompound and physical properties of such a polymer have also been unknown.

The object of the present invention is to provide a novel polymerizable polyfluoronorbornane derivative and its production process, a novel polymer obtained by polymerizing the polymerizable polyfluoronorbornane derivative, and an intermediate useful for the production of the fluorocompound.

Means to Accomplish the Object

The present invention has been made as a result of extensive studies to accomplish the above object, and it provides the followings:

1. A compound represented by the following formula (1):

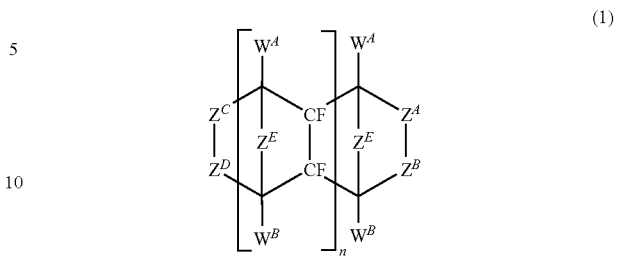

wherein the symbols in the formula have the following meanings:

$Z^A$, $Z^B$, $Z^C$, $Z^D$, and $Z^E$: each of them is independently —CH(—OC(O)CT=$CH_2$)—, —CF(—$CH_2$OC(O)CT=$CH_2$)— or —$CR^AR^B$—, provided that at least one of $Z^A$ to $Z^E$ is —CH(—OC(O)CT=$CH_2$)— or —CF(—$CH_2$OC(O)CT=$CH_2$)—, and at least one of $Z^A$ to $Z^E$ is —$CR^AR^B$— (wherein each of $R^A$ and $R^B$ is independently a fluorine atom, a $C_{1-16}$ perfluoroalkyl group or a $C_{1-16}$ perfluoroalkyl group containing an etheric oxygen atom, T is a hydrogen atom, a fluorine atom, a $C_{1-3}$ alkyl group or a $C_{1-3}$ fluoroalkyl group);

$W^A$ and $W^B$: each of them is independently a fluorine atom, a $C_{1-16}$ perfluoroalkyl group or a $C_{1-16}$ perfluoroalkyl group containing an etheric oxygen atom; and n: 0, 1 or 2.

2. A compound represented by the following formula (1A-1):

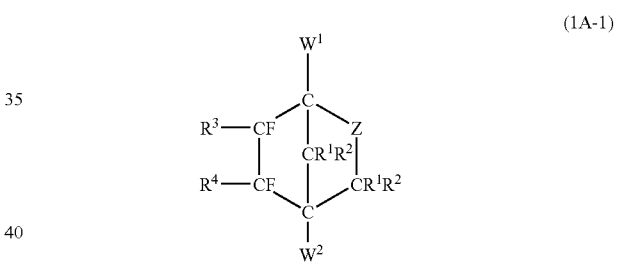

wherein the symbols in the formula have the following meanings:

Z: —CH(—OC(O)$CT^1$=$CH_2$)— or —CF(—$CH_2$OC(O)$CT^1$=$CH_2$)— (wherein $T^1$ is a hydrogen atom, a fluorine atom, a methyl group or a trifluoromethyl group);

$W^1$ and $W^2$: each of them is independently a fluorine atom or a trifluoromethyl group; and $R^1$, $R^2$, $R^3$ and $R^4$: each of them is independently a fluorine atom or a $C_{1-16}$ perfluoroalkyl group.

3. A compound selected from either one of compounds represented by the following formulae:

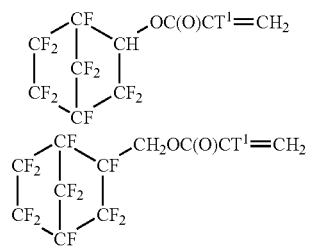

wherein $T^1$ represents a hydrogen atom, a fluorine atom, a methyl group or a trifluoromethyl group.

4. A process for producing a compound represented by the following formula (1), which comprises reacting a compound represented by the following formula (2) with a compound represented by $CH_2=CTC(O)J$:

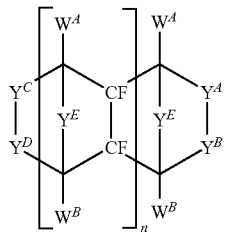
(2)

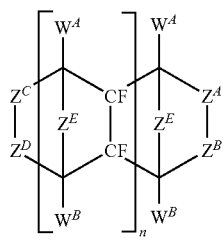
(1)

wherein the symbols in the formulae have the following meanings:

$Y^A$, $Y^B$, $Y^C$, $Y^D$, and $Y^E$: each of them is independently —CH(—OH)—, —CF(CH$_2$OH)— or —CR$^A$R$^B$—, provided that at least one of $Y^A$ to $Y^E$ is —CH(—OH)— or —CF(CH$_2$OH)—, and at least one of $Y^A$ to $Y^E$ is —CR$^A$R$^B$—; and $Z^A$, $Z^B$, $Z^C$, $Z^D$, and $Z^E$: each of them is independently —CH(—OC(O)CT=CH$_2$)—, —CF(—CH$_2$OC(O)CT=CH$_2$)— or —CR$^A$R$^B$—, provided that at least one of $Z^A$ to $Z^E$ is —CH(—OC(O)CT=CH$_2$)— or —CF(—CH$_2$OC(O)CT=CH$_2$)—, and at least one of $Z^A$ to $Z^E$ is —CR$^A$R$^B$—; wherein $Y^A$ corresponds to $Z^A$, $Y^B$ to $Z^B$, $Y^C$ to $Z^C$, $Y^D$ to $Z^D$ and $Y^E$ to $Z^E$, respectively; when each of $Z^A$ to $Z^E$ is —CH(—OC(O)CT=CH$_2$)—, each of $Y^A$ to $Y^E$ is —CH(—OH)—; when each of $Z^A$ to $Z^E$ is —CF(—CH$_2$OC(O)CT=CH$_2$)—, each of $Y^A$ to $Y^E$ is —CF(CH$_2$OH)—; and when each of $Z^A$ to $Z^E$ is —CR$^A$R$^B$—, each of $Y^A$ to $Y^E$ is —CR$^A$R$^B$—; each of R$^A$ and R$^B$ is independently a fluorine atom, a $C_{1-16}$ perfluoroalkyl group or a $C_{1-16}$ perfluoroalkyl group containing an etheric oxygen atom; and T is a hydrogen atom, a fluorine atom, a $C_{1-3}$ alkyl group or a $C_{1-3}$ fluoroalkyl group;

$W^A$ and $W^B$: each of them is independently a fluorine atom, a $C_{1-16}$ perfluoroalkyl group or a $C_{1-16}$ perfluoroalkyl group containing an etheric oxygen atom;

J: a halogen atom; and n: 0, 1 or 2.

5. A polymer which is obtained by polymerizing a compound represented by the formula (1).

6. The polymer according to 5, wherein its molecular weight is from $1 \times 10^3$ to $1 \times 10^7$.

7. A compound represented by the following formula (2):

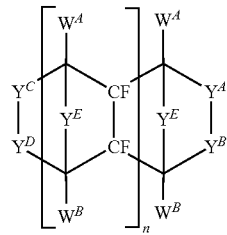
(2)

wherein the symbols in the formula have the following meanings:

$Y^A$, $Y^B$, $Y^C$, $Y^D$, and $Y^E$: each of them is independently —CH(—OH)—, —CF(CH$_2$OH)— or —CR$^A$R$^B$—, provided that at least one of $Y^A$ to $Y^E$ is —CH(—OH)— or —CF(CH$_2$OH)—, and at least one of $Y^A$ to $Y^E$ is —CR$^A$R$^B$— (wherein each of R$^A$ and R$^B$ is independently a fluorine atom, a $C_{1-16}$ perfluoroalkyl group or a $C_{1-16}$ perfluoroalkyl group containing an etheric oxygen atom);

$W^A$ and $W^B$: each of them is independently a fluorine atom, a $C_{1-16}$ perfluoroalkyl group or a $C_{1-16}$ perfluoroalkyl group containing an etheric oxygen atom; and n: 0, 1 or 2.

8. A compound represented by the following formula (2A-1):

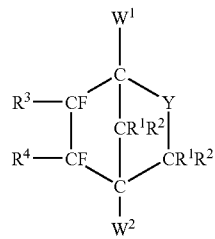
(2A-1)

wherein the symbols in the formula have the following meanings:

Y: —CH(—OH)— or —CF(—CH$_2$OH)—;

$R^1$, $R^2$, $R^3$ and $R^4$: each of them is independently a fluorine atom or a $C_{1-16}$ perfluoroalkyl group; and $W^1$ and $W^2$: each of them is independently a fluorine atom or a trifluoromethyl group.

9. A compound selected from compounds represented by the following formulae:

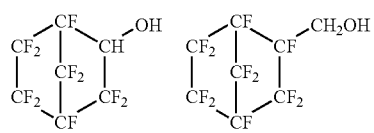

10. A process for producing a compound represented by the following formula (2), which comprises subjecting a compound represented by the following formula (3) to a reduction reaction:

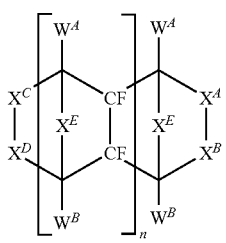

(3)

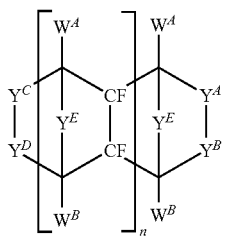

(2)

wherein the symbols in the formulae have the following meanings:

$X^A$, $X^B$, $X^C$, $X^D$ and $X^E$: each of them is independently —C(O)—, —CF(C(O)G)- or —$CR^AR^B$—, provided that at least one of $X^A$ to $X^E$ is —C(O)— or —CF(—C(O)G)-, and at least one of $X^A$ to $X^E$ is —$CR^AR^B$—;

$Y^A$, $Y^B$, $Y^C$, $Y^D$, and $Y^E$: each of them is independently —CH(—OH)—, —CF(CH$_2$OH)— or —$CR^AR^B$—, provided that at least one of $Y^A$ to $Y^E$ is —CH(—OH)— or —CF(CH$_2$OH)—, and at least one of $Y^A$ to $Y^E$ is —$CR^AR^B$—; wherein $X^A$ corresponds to $Y^A$, $X^B$ to $Y^B$, $X^C$ to $Y^C$, $X^D$ to $Y^D$ and $X^E$ to $Y^E$, respectively; when each of $Y^A$ to $Y^E$ is —CH(—OH)—, each of $X^A$ to $X^D$ is —C(O)—; when each of $Y^A$ to $Y^E$ is —CF(—CH$_2$OH)—, each of $X^A$ to $X^D$ is —CF(—C(O)G)-; and when each of $Y^A$ to $Y^E$ is —$CR^AR^B$— each of $X^A$ to $X^D$ is —$CR^AR^B$—; each of $R^A$ and $R^B$ is independently a fluorine atom, a $C_{1-16}$ perfluoroalkyl group or a $C_{1-16}$ perfluoroalkyl group containing an etheric oxygen atom; G is a halogen atom or a $C_{1-10}$ alkoxy group;

$W^A$ and $W^B$: each of them is independently a fluorine atom, a $C_{1-16}$ perfluoroalkyl group or a $C_{1-16}$ perfluoroalkyl group containing an etheric oxygen atom; and n: 0, 1 or 2.

11. A compound represented by the following formula (3):

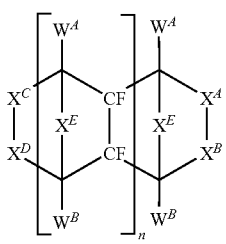

(3)

wherein the symbols in the formula have the following meanings:

$X^A$, $X^B$, $X^C$, $X^D$ and $X^E$: each of them is independently —C(O)—, —CF(C(O)G)- or —$CR^AR^B$—, provided that at least one of $X^A$ to $X^E$ is —C(O)— or —CF(—C(O)G)-, and at least one of $X^A$ to $X^E$ is —$CR^AR^B$— (wherein G is a halogen atom or a $C_{1-10}$ alkoxy group; and each of $R^A$ and $R^B$ is independently a fluorine atom, a $C_{1-16}$ perfluoroalkyl group or a $C_{1-16}$ perfluoroalkyl group containing an etheric oxygen atom);

$W^A$ and $W^B$: each of them is independently a fluorine atom, a $C_{1-16}$ perfluoroalkyl group or a $C_{1-16}$ perfluoroalkyl group containing an etheric oxygen atom; and n: 0, 1 or 2.

12. A compound represented by the following formula (3A-1):

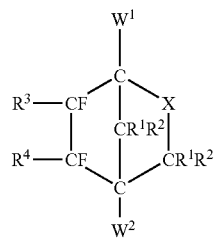

(3A-1)

wherein the symbols in the formula have the following meanings:

X: —C(O)—, —CF(C(O)F)— or —CF(C(O)OCH$_3$)—;

$R^1$, $R^2$, $R^3$ and $R^4$: each of them is independently a fluorine atom or a $C_{1-16}$ perfluoroalkyl group; and $W^1$ and $W^2$: each of them is independently a fluorine atom or a trifluoromethyl group.

13. A compound selected from compounds represented by the following formulae.

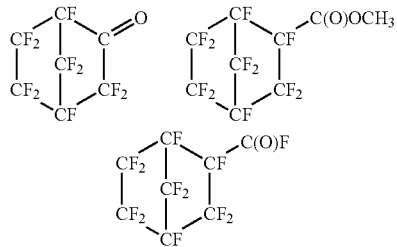

EFFECTS OF THE INVENTION

According to the present invention, a novel polymerizable polyfluoronorbornane derivative is provided. Further, by polymerizing the polyfluoronorbornane derivative, it is possible to obtain a polymer excellent in heat resistance, mold releasability, chemical resistance, transparency, light resistance, water and oil repellency, low refractive index property, etc. Particularly, it is possible to obtain a fluoropolymer excellent in dynamic water and oil repellency. Further, according to the present invention, a novel alcohol compound and a novel carbonyl compound useful as an intermediate for production of the polyfluoronorbornane derivative and for other applications, are provided.

BEST MODE FOR CARRYING OUT THE INVENTION

In the present specification, a compound represented by the formula (1) is shown as a compound (1). A group represented by —CH(—OC(O)CT=CH$_2$)— is simply shown as —CH(—OC(O)CT=CH$_2$)—. Compounds and groups represented by other formulae are shown in the same manner. Further, the meanings of the symbols in a group are the same as the previous ones unless otherwise specified.

Further, when a compound in the present invention has an asymmetric carbon atom, the steric configuration of the carbon atom is not particularly limited. With respect to a crosslinked cyclic compound in the present invention, the steric configuration of the asymmetric center on the main ring may be endo or exo. When a carbon atom on a main bridge of the crosslinked cyclic compound of the present invention forms an asymmetric center, the steric configuration of the asymmetric center may be syn or anti.

The present invention provides the following novel compound (1):

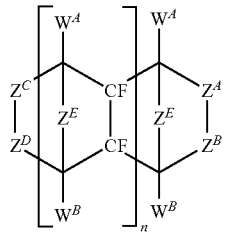

(1)

Each of $Z^A$ to $Z^E$ is a divalent linking group selected from —CH(—OC(O)CT=CH$_2$)—, —CF(—CH$_2$OC(O)CT=CH$_2$)— and —CR$^A$R$^B$—. Each of 1 to 4 groups selected from $Z^A$ to $Z^E$ is —CH(—OC(O)CT=CH$_2$)— or —CF(—CH$_2$OC(O)CT=CH$_2$)—, and each of 1 to 4 groups selected from the rest of $Z^A$ to $Z^E$ is —CR$^A$R$^B$—. Further, each of $Z^A$ to $Z^E$ is an independent group, and they may be the same or different. For example, when at least two of $Z^A$ to $Z^E$ are —CH(—OC(O)CT=CH$_2$)—, the two —CH(—OC(O)CT=CH$_2$)— may be the same groups or different groups.

Further, when at least two $Z^E$s are present in the formula (e.g. when n is 1 or 2), $Z^E$s may be the same or different, and they are preferably the same.

T is preferably a hydrogen atom, a fluorine atom, a methyl group or a trifluoromethyl group. T is particularly preferably a hydrogen atom or a methyl group, especially preferably a methyl group.

Each of $R^A$ and $R^B$ is independently preferably a fluorine atom or a $C_{1-16}$ perfluoroalkyl group. The $C_{1-16}$ perfluoroalkyl group is preferably a $C_{1-6}$ linear perfluoroalkyl group, particularly preferably a trifluoromethyl group. Further, it is particularly preferably a $C_{1-16}$ perfluoroalkyl group wherein both of $R^A$ and $R^B$ are fluorine atoms or $C_{1-16}$ perfluoroalkyl groups, or one of them is a fluorine atom and the other is a $C_{1-16}$ perfluoroalkyl group. That is, —CR$^A$R$^B$— is preferably —CF$_2$—, —C(R$^F$)$_2$— or —CFR$^F$—. R$^F$ means a $C_{1-16}$ perfluoroalkyl group (the same applies hereinafter).

With respect to $Z^A$ to $Z^E$, one or two of them are preferably groups selected from —CH(—OC(O)CT=CH$_2$)— and —CF(—CH$_2$OC(O)CT=CH$_2$)—, and the rest of three or four of is them are preferably —CR$^A$R$^B$—. Particularly preferred is that one of them is —CH(—OC(O)CT=CH$_2$)— or —CF(—CH$_2$OC(O)CT=CH$_2$)—, and the rest of four are —CR$^A$R$^B$—.

Further, as $Z^A$ to $Z^E$, the following modes are preferred.

$Z^A$ is —CH(—OC(O)CT=CH$_2$)— or —CF(—CH$_2$OC(O)CT=CH$_2$)—, and each of $Z^B$ to $Z^E$ is —CR$^A$R$^B$—; each of $Z^A$ and $Z^B$ is —CH(—OC(O)CT=CH$_2$)— or —CF(—CH$_2$OC(O)CT=CH$_2$)—, and each of $Z^C$ to $Z^E$ is —CR$^A$R$^B$—; each of $Z^A$ and $Z^C$ is —CH(—OC(O)CT=CH$_2$)— or —CF(—CH$_2$OC(O)CT=CH$_2$)—, and each of $Z^B$, $Z^D$ and $Z^E$ is —CR$^A$R$^B$—.

With respect to $Z^A$ to $Z^E$, particularly preferred is that $Z^A$ is —CH(—OC(O)CT=CH$_2$)— or —CF(—CH$_2$OC(O)CT=CH$_2$)—, and each of $Z^B$ to $Z^E$ is —CR$^A$R$^B$—.

Especially, when $Z^E$ is —CR$^A$R$^B$—, $Z^E$ is preferably —CF$_2$— or —C(RF)$_2$—, particularly preferably —CF$_2$— or —C(CF$_3$)$_2$—.

$W^A$ and $W^B$ are preferably such that each of them is a fluorine atom, or one of them is a fluorine atom and the other is a trifluoromethyl group.

n shows a repeating number of the structural unit enclosed by parenthesis [ ]. When n is 0, the compound (1) is the following compound (1A), and when n is 1, the compound (1) is the following compound (1B). When n is 2, the compound (1) is the following compound (1C).

n is preferably 0. That is, the compound (1) of the present invention is preferably the following compound (1A).

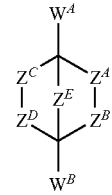

(1A)

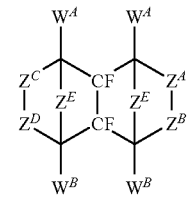

(1B)

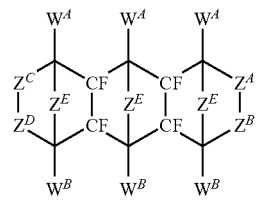

(1C)

The steric configuration of the asymmetric center on the main ring of the compound (1), is not particularly limited, and it may be endo or exo. When a carbon atom on the main bridge (a carbon atom in a group represented by $Z^E$) of the compound (1) forms the asymmetric center, the steric configuration of the asymmetric center is not particularly limited, and it may be syn or anti.

Further, the compound (1A) is preferably the following compound (1A-1), the following compound (1A-2) or the following compound (1A-3), particularly preferably the following compound (1A-1).

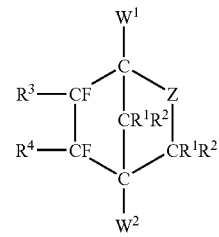

(1A-1)

(IA-2)

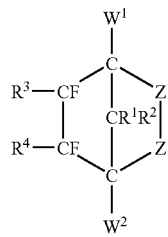

(IA-3)

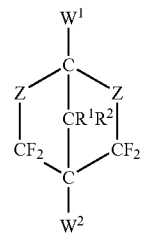

Z may be —CH(—OC(O)CT$^1$=CH$_2$)— or —CF(—CH$_2$OC(O)CT$^1$=CH$_2$)—. Further, two Z in the compound (1A-2) or the compound (1A-3) may be the same or different.

When at least two R$^1$ and R$^2$ are respectively present in the formula, they may be the same or different, and they are preferably the same. Each of R$^1$ and R$^2$ is preferably a fluorine atom or a trifluoromethyl group.

R$^3$ and R$^4$ are preferably such that each of them is a fluorine atom, or one of them is a fluorine atom and the other is a fluorine atom or a C$_{1-16}$ perfluoroalkyl group.

W$^1$ and W$^2$ are preferably such that each of them is a fluorine atom, or one of them is a fluorine atom and the other is a trifluoromethyl group.

T$^1$ is preferably a hydrogen atom or a methyl group.

Specific examples of the compound (1) may be the following compounds:

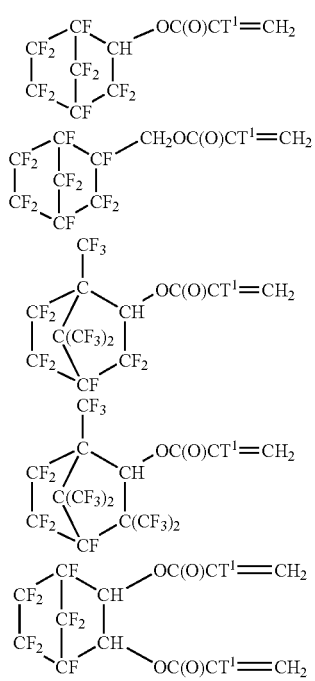

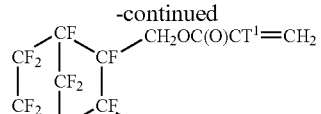

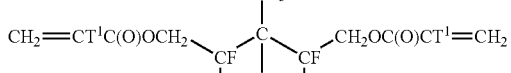

The compound (1) can be produced by reacting the following compound (2) with a compound represented by CH$_2$=CTC(O)J. The compound (2) will be described later.

(2)

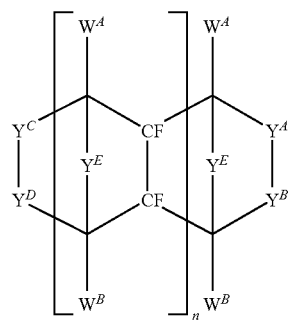

J is preferably a chlorine atom or a bromine atom.

Specific examples of the compound represented by CH$_2$=CTC(O)J may be CH$_2$=CHC(O)Cl, CH$_2$=CHC(O)Br, CH$_2$=C(CH$_3$)C(O)Cl, CH$_2$=C(CH$_3$)C(O)Br, CH$_2$=CFC(O)Cl, CH$_2$=CFC(O)Br, CH$_2$=C(CF$_3$)C(O)Cl and CH$_2$=C(CF$_3$)C(O)Br.

In the production of the compound (1), it is preferred to react from 1 k to 2 k mol of the compound represented by CH$_2$=CTC(O)J with 1 mol of the compound (2) having k number in total of —CH(—OH)— and —CF(—CH$_2$OH)— per molecule. k is an integer of from 1 to (4+n) (the same applies hereinafter).

The reaction conditions (reaction temperature, reaction pressure, reaction time, etc.) for the above reaction are not particularly limited, and it is preferred to follow a method and conditions known for an esterification reaction.

The compound (1) is a polymerizable compound having —CH(—OC(O)CT=CH$_2$)— or —CF(—CH$_2$OC(O)CT=CH$_2$)— and having a highly fluorinated norbornane structure. Therefore, a polymer can be produced by polymerizing the compound (1).

Further, the present invention provides a polymer obtained by polymerizing the compound (1). The polymer of the present invention may be a homopolymer obtained by homopolymerizing the compound (1) alone and may be a copolymer obtained by copolymerizing the compound (1) with another monomer (hereinafter referred to as another monomer) copolymerizable with the compound (1). In the latter case, the polymer of the present invention preferably contains from 0.1 to 99.9 mol % of repeating units of the compound (1) and from 0.1 to 99.9 mol % of repeating units of another monomer, based on the entire repeating units. Further, the copolymer preferably contains at least 50 to 99.9 mol % of repeating units of the compound (1) and less than 0.1 to 50 mol % of repeating units of another monomer.

Such another monomer is not particularly limited, and it may, for example, be a (meth)acrylate, an unsaturated carboxylic amide, a styrene, a vinylsilane, an olefin, a fluoroolefin, a chloroolefin, a vinyl ester, a vinyl ether, (meth)acrylic acid or acrylonitrile.

Specific examples of the (meth)acrylate may be an acyclic alkyl (meth)acrylate such as methyl (meth)acrylate, ethyl (meth)acrylate, butyl (meth)acrylate, 2-ethylhexyl (meth) acrylate, isooctyl (meth)acrylate, isononyl (meth)acrylate, decyl (meth)acrylate, octadecyl (meth)acrylate, diethylaminoethyl (meth)acrylate, 2-hydroxyethyl (meth)acrylate or 2-hydroxypropyl (meth)acrylate; and an acyclic alkyl (meth) acrylate such as 1-adamantyl (meth)acrylate, 3-hydroxyl-1-adamantyl (meth)acrylate, 2-methyl-2-adamantyl (meth) acrylate, 2-ethyl-2-adamantyl (meth)acrylate, 2-propyl-2-adamantyl (meth)acrylate, 2-butyl-2-adamantyl (meth) acrylate, 2-oxotetrahydrofuran-3-yl (meth)acrylate, glycidyl (meth)acrylate or benzyl (meth)acrylate.

Specific examples of the unsaturated carboxylic amide may be acrylamide, diamide itaconate, α-ethyl acrylamide, amide crotonate, diamide fumarate, diamide maleate, N-butoxymethyl acrylamide and N-methylol-acrylamide.

Specific examples of the styrene may be styrene, α-methylstyrene, chlorostyrene and hydroxystyrene.

Specific examples of the vinylsilane may be vinyl methyl dimethoxysilane, vinyl methyl diethoxysilane, vinyl methyl dichlorosilane, vinyl trimethoxysilane, vinyl triethoxysilane and vinyl trichlorosilane.

Specific examples of the olefin may be ethylene, propylene and isobutylene.

Specific examples of the fluoroolefin may be an acyclic fluoromonoene such as vinyl fluoride, vinylidene fluoride, tetrafluoroethylene or hexafluoropropylene; a cyclic fluoromonoene such as perfluoro(2,2-dimethyl-1,3-dioxole) or perfluoro(2-methylene-1,3-dioxolane); and a fluorodiene such as $CF_2=CFOCF_2CF_2CF=CF_2$, $CF_2=CFOCF_2CF(CF_3)CF=CF_2$, $CF_2=CFOCF(CF_3)CF_2CF=CF_2$, $CF_2=CFCF_2C(CF_3)(OH)CH_2CH=CH_2$ or $CF_2=CFCH_2CH(C(CF_3)_2OH)CH_2CH=CH_2$.

Specific examples of the chloroolefin may be vinyl chloride, vinylidene chloride and chloroprene.

Specific examples of the vinyl ester may be vinyl acetate and vinyl propionate.

Specific examples of the vinyl ether may be 2-hydroxyvinyl ether and aminoethyl vinyl ether.

The polymerization of the compound (1) is preferably carried out in the presence of a polymerization initiator. Specific examples of the polymerization initiator may be an organic peroxide such as $(C_6H_5C(O)O-)_2$, $(C_6F_5C(O)O-)_2$, $(C_3F_7C(O)O-)_2$, $((CH_3)_3CC(O)-)_2$, $((CH_3)_2CHC(O)O-)_2$, $((CH_3)_3C(O)C(O)O-)_2$, $((CH_3)_3C(O)O-)_2$, $((CH_3)_2CHOC(O)O-)_2$ or $((CH_3)_3CC_6H_{10}OC(O)O-)_2$, an azo compound such as azobisisobutyronitrile, and an inorganic peroxide.

The polymerization conditions (polymerization temperature, polymerization pressure, etc.) in the polymerization of the compound (1) are not particularly limited. The polymerization temperature is preferably from 0 to 200° C. The polymerization pressure is preferably from atmospheric pressure to 10 MPa (gauge pressure).

The weight average molecular weight of the polymer of the present invention is preferably from $1\times10^3$ to $1\times10^7$, more preferably from $1\times10^3$ to $1\times10^5$.

The polymer of the present invention is a polymer excellent in transparency, water and oil repellency, heat resistance, mold releasability, chemical resistance and particularly dynamic water repellency. The polymer of the present invention is useful as an antifouling agent, a water and oil repellent, a mold lubricant, an optical fiber material, a pellicle material, a lens material, a surface protecting material for a display.

Further, the preferred mode of the polymer of the present invention may be a polymer which is obtained by homopolymerizing the compound (1) alone, and which is made of only repeating units of the compound (1) and has a weight average molecular weight of from 1,000 to 50,000. The repeating units in the present specification mean units formed by polymerization of a polymerizable compound such as the compound (1).

The following compound (2) as an intermediate for production of the compound (1) is a novel compound having a hydroxyl group or a hydroxymethyl group and having a highly fluorinated norbornane structure. In addition to being useful as an intermediate for production of the compound (1), the compound (2) can be converted to various derivatives by utilizing the reactivity of hydroxyl groups in $Y^A$ to $Y^E$. Since every converted compound has a highly fluorinated norbornane structure, the compound exhibits performance such as water and oil repellency, which is derived from the structure. That is, the present invention provides the following novel compound (2).

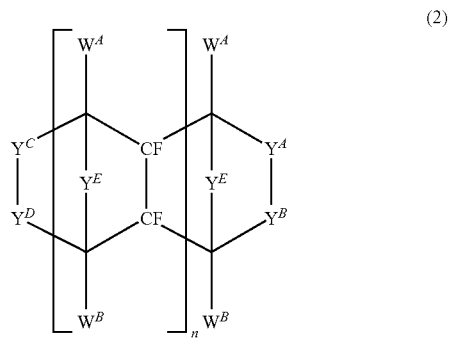

(2)

$Y^A$, $Y^B$, $Y^C$, $Y^D$, and $Y^E$ are as defined above, and their preferred modes are as follows.

$Y^A$ is —CH(—OH)— or —CF(—CH$_2$OH)—, and each of $Y^B$, $Y^C$, $Y^D$ and $Y^E$ is —CR$^A$R$^B$—; each of $Y^A$ and $Y^B$ is —CH(—OH)— or —CF(—CH$_2$OH)—, and each of $Y^C$, $Y^D$ and $Y^E$ is —CR$^A$R$^B$—; and each of $Y^A$ and $Y^C$ is —CH(—OH)— or —CF(—CH$_2$OH)—, and each of $Y^B$, $Y^D$ and $Y^E$ is —CR$^A$R$^B$—.

Further, it is particularly preferred that $Y^A$ is —CH(—OH)— or —CF(—CH$_2$OH)—, and each of $Y^B$, $Y^C$, $Y^D$ and $Y^E$ is —CR$^A$R$^B$—.

Here, $R^A$ and $R^B$ are as defined above, and they may be the same or different. Each of $R^A$ and $R^B$ is independently preferably a fluorine atom or a $C_{1-16}$ perfluoroalkyl group. Particularly preferred is that both of them are fluorine atoms or $C_{1-16}$ perfluoroalkyl groups, or that one of them is a fluorine atom, and the other is a $C_{1-16}$ perfluoroalkyl group. That is, —CR$^A$R$^B$— is preferably —CF$_2$—, —C(R$^F$)$_2$— or —CFR$^F$—.

When $Z^E$ is —CR$^A$R$^B$—, $Z^E$ is preferably —CF$_2$— or —C(RF)$_2$—, particularly preferably —CF$_2$— or —C(CF$_3$)$_2$—.

$W^A$ and $W^B$ are independent of each other, and they may be the same or different. When at least two $W^A$s are present in a molecule, they may be the same or different. The same applies to $W^B$. $W^A$ and $W^B$ are preferably such that each of them is a fluorine atom, or one of them is a fluorine atom and the other is a trifluoromethyl group.

n has the same meaning as above, and n is preferably 0. When n is 0, the compound (2) is the following compound (2A), and when n is 1, the compound (2) is the following compound (2B). When n is 2, the compound (2) is the following compound (2C).

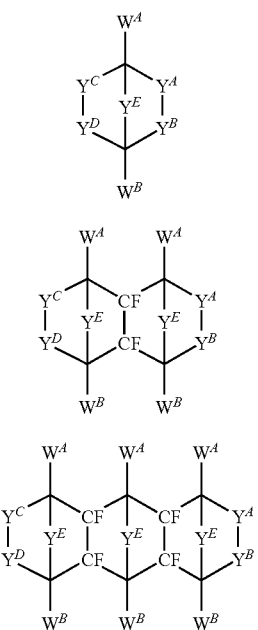

(2A)

(2B)

(2C)

The steric configuration of the asymmetric center on the main ring of the compound (2) is not particularly limited, and it may be endo or exo. When a carbon atom on the main bridge (a carbon atom in a group represented by $Y^E$) of the compound (2) forms the asymmetric center, the steric configuration of the symmetric center is not particularly limited, and it may be syn or anti.

The compound (2) is preferably the following compound (2A-1), the following compound (2A-2) or the following compound (2A-3), particularly preferably the following compound (2A-1).

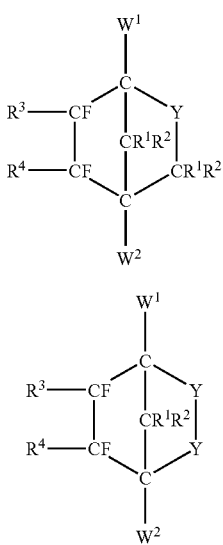

(2A-1)

(2A-2)

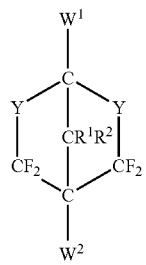

(2A-3)

Y is —CH(—OH)— or —CF(—CH$_2$OH)—. Two Ys in the compound (2A-2) or the compound (2A-2) may be the same or different.

Each of $R^1$ and $R^2$ is preferably a fluorine atom or a trifluoromethyl group.

$R^3$ and $R^4$ are preferably such that each of them is a fluorine atom, or one of them is a fluorine atom and the other is a fluorine atom or a $C_{1-16}$ perfluoroalkyl group.

$W^1$ and $W^2$ are preferably such that each of them is a fluorine atom, or one of them is a fluorine atom and the other is a trifluoromethyl group.

Specific examples of the compound (2) may be the following compounds.

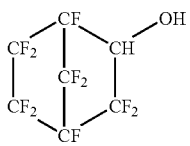 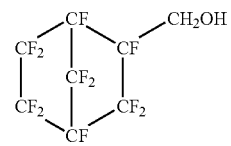

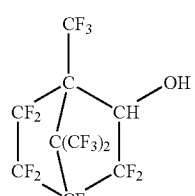 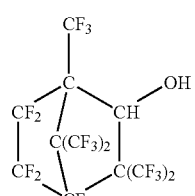

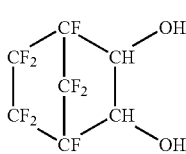 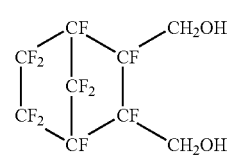

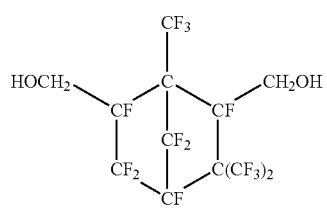

The compound (2) can be produced by subjecting the following compound (3) to a reduction reaction. The detail of the compound (3) will be described later.

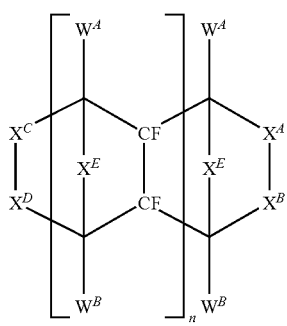

(3)

The reduction reaction of the compound (3) is preferably carried out by a reaction between the compound (3) with a reducing agent. The reducing agent is not particularly limited, and it is preferably $NaBH_4$, a tetrahydrofuran solution of $B_2H_6$, a hexane solution of $((CH_3)_2CHCH_2)_2AlH$, or $LiAlH_4$.

The reduction reaction is preferably carried out by reacting from 1 k to 2 k mol of the reducing agent with 1 mol of the compound (3) having k number in total of —C(O)— and —CF(—C(O)G)- in one molecule.

The reaction conditions (reaction temperature, reaction pressure, reaction time, etc.) for the reduction reaction are not particularly limited. For example, it is preferably carried out in accordance with a method described in a paragraph 0021 of JP-A-10-72568, wherein acyl fluoride (—COF) is esterified to methyl ester (—COOCH$_3$) or the like, followed by reduction with $NaBH_4$, to obtain an alcohol (—CH$_2$OH).

The compound (3) is a novel compound having —C(O)— or —CF(—C(O)G)- and a highly fluorinated norbornane structure. The compound (3) is useful e.g. as an intermediate for production of the compound (2). That is, the present invention provides the following novel compound (3).

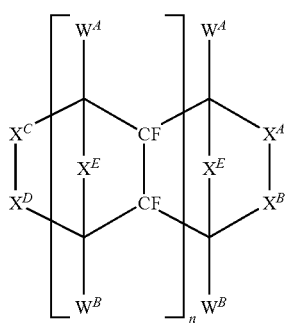

(3)

$X^A$, $X^B$, $X^C$, $X^D$ and $X^E$ are as defined above, and the following modes are preferred. That is, $X^A$ is —C(O)— or —CF(—C(O)G)-, and each of $X^B$, $X^C$, $X^D$ and $X^E$ is —CR$^A$R$^B$—; each of $X^A$ and $X^B$ is —C(O)— or —CF(—C(O)G)-, and each of $X^C$, $X^D$ and $X^E$ is —CR$^A$R$^B$—; each of $X^A$ and $X^C$ is —C(O)— or —CF(—C(O)G)-, and each of $X^B$, $X^D$ and $X^E$ is —CR$^A$R$^B$—. Further, particularly preferred is that $X^A$ is —C(O)— or —CF(—C(O)G)-, and that each of $X^B$, $X^C$, $X^D$ and $X^E$ is —CR$^A$R$^B$—.

G is preferably a fluorine atom or a $C_{1-10}$ alkoxy group, particularly preferably a fluorine atom or a methoxy group.

Each of $R^A$ and $R^B$ is independently preferably a fluorine atom or a $C_{1-16}$ perfluoroalkyl group. Particularly preferred is that both of them are fluorine atoms or $C_{1-16}$ perfluoroalkyl groups, or that one of them is a fluorine atom, and the other is a $C_{1-16}$ perfluoroalkyl group. That is, —CR$^A$R$^B$— is preferably —CF$_2$—, —C(R$^F$)$_2$— or —CFR$^F$—. Here, R$^F$ means a $C_{1-16}$ perfluoroalkyl group.

When $Z^E$ is —CR$^A$R$^B$—, $Z^E$ is preferably —CF$_2$— or —C(R$^F$)$_2$, particularly preferably —CF$_2$— or —C(CF$_3$)$_2$—.

$W^A$ and $W^B$ are preferably such that each of them is a fluorine atom, or one of them is a fluorine atom and the other is a trifluoromethyl group.

n has the same meaning as above. n is preferably 0. When n is 0, the compound (3) is the following compound (3A), and when n is 1, the compound (3) is the following compound (3B). When n is 2, the compound (3) is the following compound (3C).

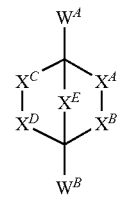

(3A)

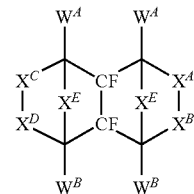

(3B)

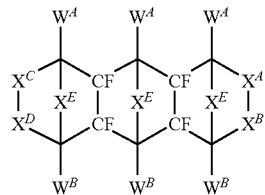

(3C)

The steric configuration of the asymmetric center on the main ring of the compound (3) is not particularly limited, and it may be endo or exo. When a carbon atom on the main bridge (a carbon atom in a group represented by $X^E$) of the compound (3) forms the asymmetric center, the steric configuration of the symmetric center is not particularly limited, and it may be syn or anti.

The compound (3) is preferably the following compound (3A-1), the following compound (3A-2) or the following compound (3A-3), particularly preferably the following compound (3A-1).

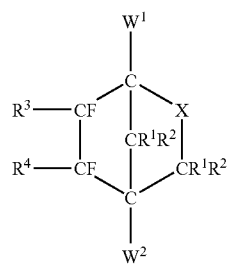

(3A-1)

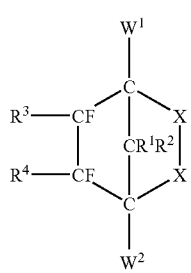

(3A-2)

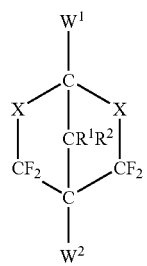

(3A-3)

X is —C(O)—, —CF(—C(O)F)— or —CF(—C(O)OCH$_3$)—. Two Xs in the compound (3A-2) or in the compound (3A-3) may be the same or different.

Each of R$^1$ and R$^2$ is preferably a fluorine atom or a trifluoromethyl group.

R$^3$ and R$^4$ are preferably such that each of them is a fluorine atom, or one of them is a fluorine atom and the other is a fluorine atom or a C$_{1-16}$ perfluoroalkyl group.

W$^1$ and W$^2$ are preferably such that each of them is a fluorine atom, or one of them is a fluorine atom and the other is a trifluoromethyl group.

Specific examples of the compound (3) may be the following compounds.

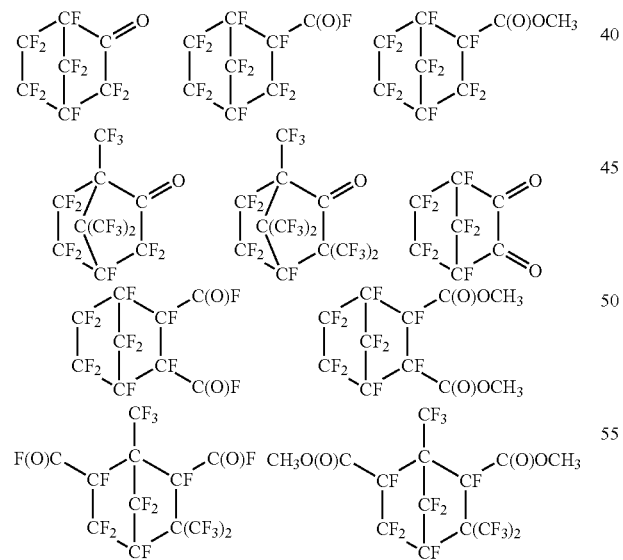

The compound (3) can be produced in such a manner that the following compound (6) and a compound represented by R$^f$—C(O)F are subjected to an esterification reaction to obtain the following compound (5), and then, the compound (5) is subjected to a fluorination reaction to obtain the following compound (4), followed by a thermal decomposition reaction of the compound (4), in the presence of an alkali metal fluoride. Further, it can also be produced by reacting the compound (4) with a C$_{1-10}$ alkanol.

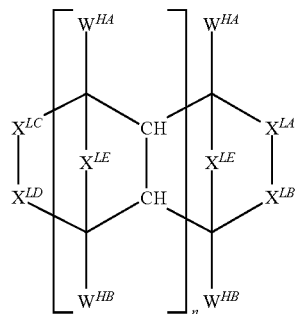

(6)

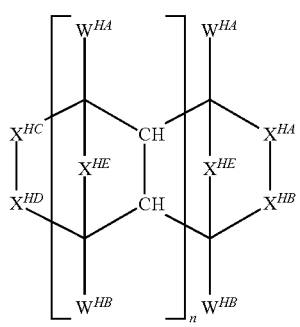

(5)

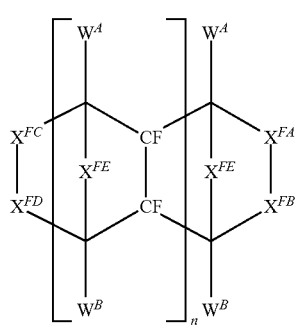

(4)

wherein the symbols in the formulae have the following meanings:

Each of X$^{FA}$, X$^{FB}$, X$^{FC}$, X$^{FD}$ and X$^{FE}$: —CF(—OC(O)R$^f$)—, —CF(—CF$_2$OC(O)R$^f$)— or —CR$^A$R$^B$—. However, X$^{FA}$ is a group corresponding to X$^A$, X$^{FB}$ to X$^B$, X$^{FC}$ to X$^C$, X$^{FD}$ to X$^D$ and X$^{FE}$ to X$^E$, respectively; a group corresponding to —C(O)— is —CF(—OC(O)R$^f$)—, a group corresponding to —C(—C(O)G)- is —CF(—CF$_2$OC(O)R$^f$)—, and a group corresponding to —CR$^A$R$^B$— is —CR$^A$R$^B$—.

Each of X$^{HA}$, X$^{HB}$, X$^{HC}$, X$^{HD}$ and X$^{HE}$: —CH(O)R$^f$)—, —CH(—CH$_2$OC(O)R$^f$— or —CR$^{HA}$R$^{HB}$—. However, X$^{HA}$ is a group corresponding to X$^{FA}$, X$^{HB}$ to X$^{FB}$, X$^{HC}$ to X$^{FC}$, X$^{HD}$ to X$^{FD}$ and X$^{HE}$ to X$^{FE}$, respectively; a group corresponding to —CF(—OC(O)R$^f$)— is —CH(—OC(O)R$^f$)—, a group corresponding to —CF(CF$_2$OC(O)R$^f$)— is —CH(—CH$_2$OC(O)R$^f$)—, and a group corresponding to —CR$^{HA}$R$^{HB}$— is —CR$^{HA}$R$^{HB}$—. Further, between X$^{HC}$ and X$^{HD}$, a carbon atom-carbon atom double bond may be formed.

Each of X$^{LA}$, X$^{LB}$, X$^{LC}$, X$^{LD}$ and X$^{LE}$: —CH(—OH)—, —CH(—CH$_2$OH)— or —CR$^{HA}$R$^{HB}$—. However, X$^{LA}$ is a group corresponding to X$^{HA}$, X$^{LB}$ to X$^{HB}$, X$^{LC}$ to X$^{HC}$, X$^{LD}$ to $X^{HD}$ and $X^{LE}$ to $X^{HE}$, respectively; a group corresponding to —CH(—OC(O)R$^f$)— is —CH(OH)—, a group corresponding to —CH(—CH$_2$OC(O)R$^f$)— is —CH(—CH$_2$OH)— and a group corresponding to —CR$^{HA}$R$^{HB}$— is —CR$^{HA}$R$^{HB}$—. Further, a carbon-carbon bond between $X^{LC}$ and $X^{LD}$ may be a double bond.

Each of W$^{HA}$ and W$^{HB}$: a hydrogen atom, a C$_{1-16}$ alkyl group or a C$_{1-16}$ alkyl group containing an etheric oxygen atom. However, W$^{HA}$ is a group corresponding to W$^A$, W$^{HB}$ to W$^B$; a group corresponding to a fluorine atom is a hydrogen atom; a group corresponding to a C$_{1-16}$ perfluoroalkyl group is a C$_{1-16}$ alkyl group; a group corresponding to a C$_{1-16}$ perfluoroalkyl group containing an etheric oxygen atom is a C$_{1-16}$ alkyl group containing an etheric oxygen atom.

Each of R$^{HA}$ and R$^{HB}$: a hydrogen atom, a C$_{1-16}$ alkyl group or a C$_{1-16}$ alkyl group containing an etheric oxygen atom. However, R$^{HA}$ is a group corresponding to R$^A$, R$^{HB}$ to R$^B$, R$^{HC}$ to R$^C$, R$^{HD}$ to R$^D$ and R$^{ED}$ to R$^E$, respectively; a group corresponding to a fluorine atom is a hydrogen atom; a group corresponding to a C$_{1-16}$ perfluoroalkyl group is a C$_{1-16}$ alkyl group; and a group corresponding to a C$_{1-16}$ perfluoroalkyl group containing an etheric oxygen atom is a C$_{1-16}$ alkyl group containing an etheric oxygen atom.

R$^f$: a C$_{1-20}$ perfluoroalkyl group or a C$_{1-20}$ perfluoroalkyl group containing an etheric oxygen atom.

Specific examples of the compound (6) may be the following compounds. The compound (6) is a known compound or a compound obtainable by a known method.

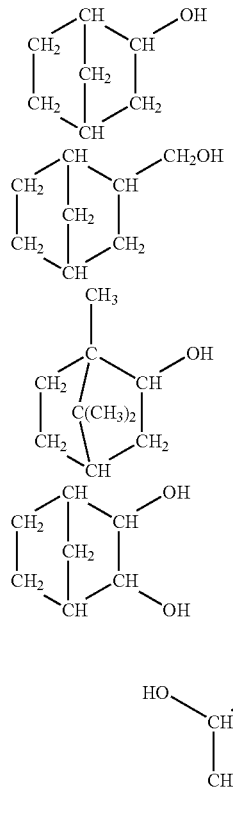

Specific examples of the compound represented by R$^f$—C(O)F may be CF$_3$C(O)F, (CF$_3$)$_2$CFC(O)F, F(CF$_2$)$_3$OCF(CF$_3$)C(O)F and F(CF$_2$)$_3$OCF(CF$_3$)CF$_2$OCF(CF$_3$)C(O)F.

Specific examples of the compound (5) may be the following compounds.

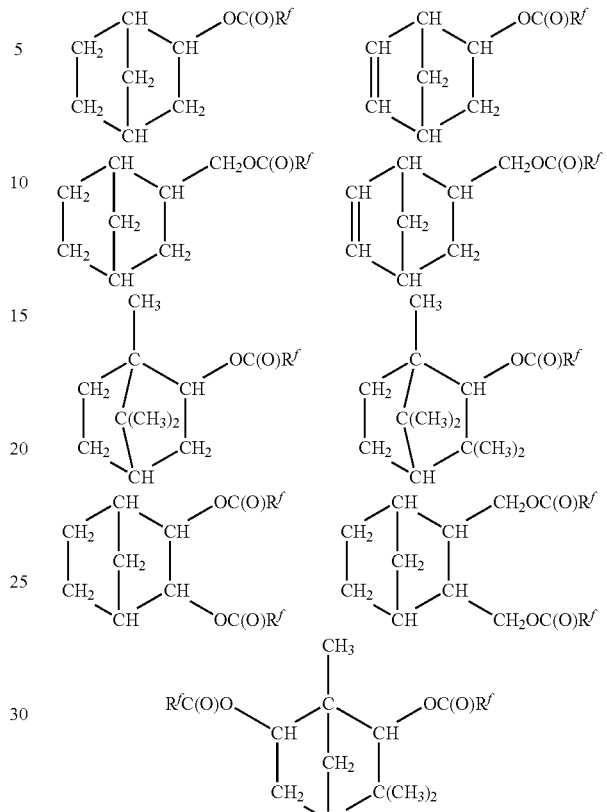

Specific examples of the compound (4) may be the following compounds.

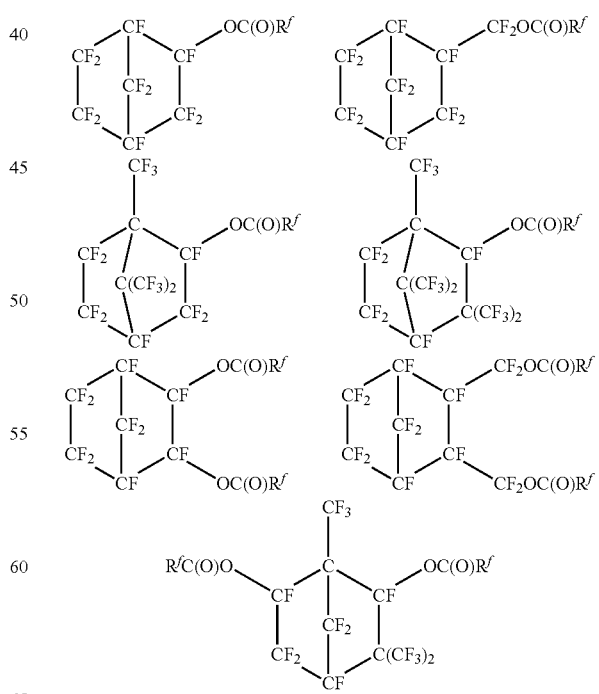

The respective reaction conditions for an esterification reaction of the compound (6) with the compound represented by $R^f$—C(O)F, a fluorination reaction of the compound (5) and a thermal decomposition reaction of the compound (4), are preferably the reaction conditions described in WO00/56694, WO02/18314, etc.

According to the present invention, a novel polymerizable compound and polymer can be provided. The polymer of the present invention has a structure wherein a highly fluorinated norbornane structure is hanged on a side chain, whereby the polymer exhibits excellent water and oil repellency, heat resistance, mold releasability, chemical resistance, transparency, durability, light resistance and low refractive index property. The polymer provided by the present invention is particularly excellent in dynamic water and oil repellency, especially excellent in dynamic water repellency, and that is, it is a polymer having an excellent property such that the contact angle with water is at least 80°, and the sliding angle is at most 20°. The polymer of the present invention is useful for various applications, in which such properties are required.

EXAMPLES

In Examples, 1,1,2-trichloro-1,2,2-trifluoroethane is shown as R113, dichloropentafluoropropane as R225, tetrahydrofuran as THF, and tetramethylsilane as TMS. As R225, a mixture of $CF_3CF_2CHCl_2$ and $CF_2ClCF_2CHFCl$, was used.

Example 1

Production Example of Compound (31)

By following a production route represented by the following formula, a compound (31) was produced from the following compound (61). Here, a compound represented by $R^{f1}$—COF is $F(CF_2)_3OCF(CF_3)CF_2OCF(CF_3)C(O)F$.

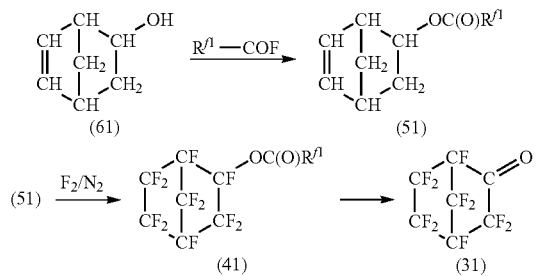

Into a flask under a nitrogen gas atmosphere, 15 g of the compound (61), 100 g of chloroform and 7.02 g of NaF were introduced, and while inside of the flask was cooled with ice and was stirred, 79 g of the compound represented by $R^{f1}$—COF was dropwise added thereto. After inside of the flask was further stirred, an insoluble solid in the content of the flask was removed by pressure filtration. Into the content of the flask, 103 g of saturated sodium hydrogen carbonate aqueous solution was added. An organic layer of the formed two-layer separated liquid was recovered. The recovered organic layer was concentrated to obtain 74 g of a compound (51).

Then, into an autoclave (made of nickel, inner volume: 500 mL) having a NaF pellet packed bed set at a gas outlet, 313 g of R113 was added, and while stirring inside of the autoclave at 25° C., nitrogen gas was blown into the autoclave for 1 hour. Further, fluorine gas diluted to 20% volume with nitrogen gas (hereinafter referred to as 20% fluorine gas) was blown therein.

While the 20% fluorine gas was continuously blown therein, under a pressure of 0.1 MPa (gauge pressure), a solution having 67 g of the compound (51) dissolved in 299 g of R113, was introduced in the autoclave. After completion of the introduction, nitrogen gas was blown into the autoclave. Then, the content in the autoclave was recovered and concentrated to obtain a compound (41).

Then, into a flask under a nitrogen gas atmosphere, 80 g of the compound (41) and 0.7 g of a KF powder were introduced, and while the inner temperature of the flask was raised to from 80 to 120° C., the flask was heated for 6 hours. The content of the flask was purified by using a distillation method using a cold trap and a recrystallization method, to obtain 38 g of white solid compound (31).

The NMR data of the compound (31) are shown as follows.
$^{19}$F-NMR (282.7 MHz, solvent: $CDCl_3$, standard: $CFCl_3$) δ (ppm): −116.8 (1F), −118.2 (1F), −122.9 (1F), −123.3 (1F), −125.4 (1F), −127.3 (1F), −130.6 (1F), −134.6 (1F), −219.4 (1F), −227.5 (1F).

Example 2

Production Example of Compound (21)

Into a round-bottom flask (inner volume: 100 mL) under a nitrogen gas atmosphere, 1.1 g of $NaBH_4$ and 30 g of THF were introduced. While the flask was cooled with ice and was stirred, 48 g of an R225 solution containing 22 mass % of the compound (31) was dropwise added into the flask, over 1.5 hours. After completion of the dropwise addition, inside of the flask was stirred for further 30 minutes. Further, while keeping the inner temperature of the flask at 25° C., inside of the flask was stirred for 12 hours. Then, the liquid content of the flask was neutralized with 0.1 mol/L of a hydrochloric acid aqueous solution (150 mL), followed by washing with water. The resultant was distilled and purified to obtain the following compound (21).

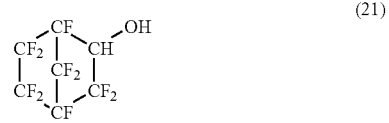

The NMR data of the compound (21) are shown as follows.
$^1$H-NMR (300.4 MHz, solvent: $CDCl_3$, standard: TMS) δ (ppm): 4.89 to 4.57 (2H).
$^{19}$F-NMR (282.7 MHz, solvent: $CDCl_3$, standard: $CFCl_3$) δ (ppm): −105.0 (1F), −119.7 (1F), −124.0 (1F), −124.3 (1F), −125.7 (1F), −126.8 (1F), −133.2 (2F), −216.6 (1F), −223.5 (1F).

Example 3

Production Example of Compound (11)

Into a flask, 2.2 g of the compound (21), 10 g of THF, 2 mg of an aluminum salt of N-nitrosophenyl hydroxyamine and 1.2 g of triethylamine were introduced. The flask was cooled with ice, and with stirring, 7.3 g of a THF solution of a compound represented by $CH_2$=$C(CH_3)C(O)Cl$ (1.2 g) was slowly dropwise added into the flask. After completion of the dropwise addition, inside of the flask was stirred for 2 hours, and then, 30 mL of a sodium hydrogencarbonate aqueous solution was added thereto.

The extraction liquid obtained by extracting the liquid content of the flask with R225, was dried over anhydrous sodium sulfate, and then, concentrated to obtain a concentrated liquid. The concentrated liquid was purified by a silica gel column chromatography to obtain 2.7 g of the following compound (11).

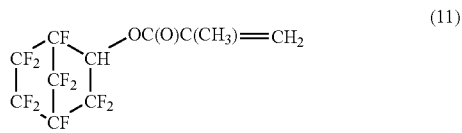

(11)

The NMR data of the compound (11) are shown as follows.
$^1$H-NMR (300.4 MHz, solvent: CDCl$_3$, standard: TMS) δ (ppm): 6.31 (1H), 5.88 (1H), 5.84 (1H), 2.01 (3H).
$^{19}$F-NMR (282.7 MHz, solvent: CDCl$_3$, standard: CFCl$_3$) δ (ppm): −104.6 (1F), −120.5 (1F), −122.4 (1F), −124.2 (1F), −124.6 (1F), −126.5 (1F), −132.7 to −132.8 (2F), −214.8 (1F), −223.2 (1F).

Example 4

Production Example of Compound (32$^M$)

By following the production route represented by the following formula, a compound (32$^M$) was produced from the following compound (62). Here, a compound represented by R$^{f2}$—C(O)F is a compound represented by F(CF$_2$)$_3$OCF(CF$_3$)C(O)F.

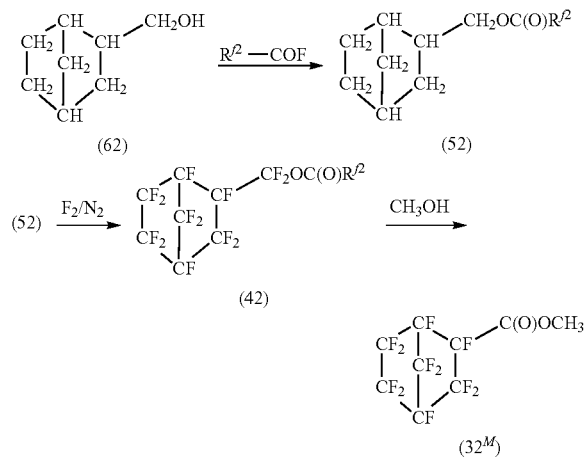

Into a flask under a nitrogen gas atmosphere, 26 g of the compound (62) and 100 g of R225 were introduced. With cooling with ice, 91 g of the compound represented by R$^{f2}$—C(O)F was dropwise added thereto while stirring inside of the flask. Inside of the flask was further stirred, and then, the content was concentrated and filtrated to obtain 88 g of compound (52).

Then, into an autoclave (made of nickel, inner volume: 500 mL) having a NaF pellet packed bed set at a gas outlet, 326 g of R113 was added, and while stirring inside of the autoclave at 25° C., a nitrogen gas was blown into the autoclave for 1 hour. Further, 20% fluorine gas was blown therein.

While the 20% fluorine gas was continuously blown therein, under a pressure of 0.1 MPa (gauge pressure), a solution having 75 g of the compound (52) dissolved in 346 g of R113, was introduced in the autoclave. After completion of the introduction, a nitrogen gas was blown into the autoclave. Then, the autoclave content was recovered and concentrated to obtain a compound (42).

Under cooling with ice, 20 g of methanol was dropwise added to a solution obtained by dissolving 106 g of the compound (42) into 100 mL of R225. After completion of the dropwise addition, at a solution temperature of 25° C., the solution was stirred for 12 hours. R225 and F(CF$_2$)$_3$OCF(CF$_3$)COOCH$_3$ were distilled from the solution to obtain 42 g of a compound (32$^M$).

The NMR data of the compound (32$^M$) are shown as follows.
$^1$H-NMR (300.4 MHz, solvent: CDCl$_3$, standard: TMS) δ (ppm): 3.97 (3H).
$^{19}$F-NMR (282.7 MHz, solvent: CDCl$_3$, standard: CFCl$_3$) δ (ppm): −116.4 to −132.2 (8F), −174.3 (1F), −219.1 (1F), −227.0 (1F).

Example 5

Production Example of Compound (32$^F$)

Into a flask having a simple distillation apparatus set on its upper part, 100 g of the compound (42) obtained in the same manner as in Example 4 and 1.7 g of a KF powder were introduced. When the inner temperature of the flask was adjusted to be at 80° C. and inside of the flask was stirred, reflux of the liquid content of the flask was observed. While having F(CF$_2$)$_3$OCF(CF$_3$)COF distilled by the simple distillation apparatus, inside of the flask was stirred for 5 hours. After completion of the distillation to the simple distillation apparatus, the flask was gradually cooled, and R225 and R113 were introduced in the flask. Then, as a result of analyzing the reaction product obtained by removing KF in the liquid content of the flask by pressure filtration, the formation of the following compound (32$^F$) was confirmed. The yield calculated from $^{19}$F-NMR was 96%.

The NMR data of the compound (32$^F$) are as follows.
$^{19}$F-NMR (282.7 MHz, solvent: CDCl$_3$, standard: CFCl$_3$) δ (ppm): +39.3 to +35.6 (1F), −117.5 to −132.0 (8F), −178.8 (1F), −218.0 to −226.2 (2F).

(32$^F$)

Example 6

Production Example of Compound (22)

Into an ice-cooled solution obtained by dissolving 42 g of the compound (32$^M$) into 100 mL of THF, 20 g of a hexane solution containing 79 mass % of ((CH$_3$)$_2$CHCH$_2$)$_2$AlH was dropwise added. After completion of the dropwise addition, the solution was stirred at 25° C. for 12 hours, and then, the solution was neutralized with 0.2 mol/L hydrochloric aqueous solution (150 mL) to obtain a reaction crude liquid.

The reaction crude liquid was extracted with R225 to obtain an extraction liquid, and a low-boiling component of the extraction liquid was distilled to obtain 31 g of a white solid reaction product. The reaction product was recrystallized in hexane to obtain the following compound (22) of a capillary crystal (colorless).

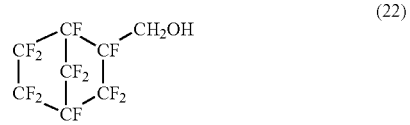
(22)

The NMR data of the compound (22) are as follows.
$^1$H-NMR (300.4 MHz, solvent: CDCl$_3$, standard: TMS) δ (ppm): 4.20 (2H, dd, j=24.9 and 6.6 Hz), 2.15 (1H, m).
$^{19}$F-NMR (282.7 MHz, solvent: CDCl$_3$, standard: CFCl$_3$) δ (ppm): −119.3 (1F), −121.3 (1F), −123.5 (1F), −123.6 (1F), −124.6 (1F), −125.0 (1F), −128.7 (1F), −131.6 (1F), −183.2 (1F), −220.2 (1F), −227.1 (1F).

Example 7

Production Example of Compound (12)

Into a flask, 16.3 g of the compound (22), 82 mL of tert-butyl methyl ether, 5 mg of hydroquinone and 8.1 g of triethylamine were introduced. While cooling inside of the flask with ice and stirring, 8.4 g of CH$_2$=C(CH$_3$)C(O)Cl was dropwise added into the flask. After completion of the dropwise addition, inside of the flask was further stirred for 17 hours, and then, 50 mL of pure water was introduced in the flask. The salt precipitated in the flask was dissolved to obtain a two-layer separated liquid.

The upper layer (a tert-butyl methyl ether layer) of the content of the flask was recovered, and the recovered liquid was dried over anhydrous sodium sulfate and was concentrated to obtain a concentrated liquid. The concentrated liquid was purified by a silica gel column chromatography to obtain 14 g of the following compound (12).

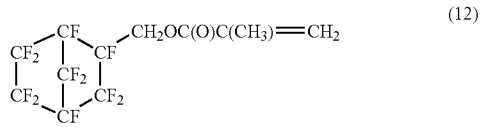
(12)

The NMR data of the compound (12) are as follows.
$^1$H-NMR (300.4 MHz, solvent: CDCl$_3$, standard: TMS) δ (ppm): 6.20 (1H), 5.70 (1H), 4.75 (2H), 1.98 (3H).
$^{19}$F-NMR (282.7 MHz, solvent: CDCl$_3$, standard: CFCl$_3$) δ (ppm): −118.6 (1F), −120.6 (1F), −123.8 (2F), −124.5 (1F), −124.9 (1F), −128.6 (1F), −131.4 (1F), −179.1 (1F), −219.8 (1F), −227.0 (1F).

Example 8

Polymerization Example of Compound (11)

Into a pressure-proof reactor (inner volume: 30 mL), 3.0 g of the compound (11), 11.3 g of R225 and 1.5 g of diisopropylperoxycarbonate which was diluted to 50 mass % by R225, were introduced. Inside of the reactor was frozen and degassed, and then, the inner temperature of the reactor was adjusted to 40° C., and a polymerization reaction was carried out for 18 hours. After the polymerization reaction, the content liquid of the reactor was dropwise added to methanol, the formed solid product was recovered, and the solid product was vacuum dried at 90° C. for 15 hours. As a result, 2.2 g of a polymer formed by polymerization of the compound (11) (hereinafter referred to as a polymer (11)) was obtained. The formation of the polymer can be confirmed according to the fact that the compound (11) could hardly be detected by an NMR measurement of the liquid content, and there was no absorption based on a methacryloyl group in IR of the product. The polymer (11) was a white solid polymer at 25° C.

The molecular weight of the polymer (11) was measured by a gel permeation chromatography method wherein a solvent mixture made of 99 vol % of R225 and 1 vol % of hexafluoropropanol, was referred to as a mobile phase, and polymethyl methacrylate was referred to as an inner standard. The number average molecular weight of the polymer (11) was 4,600, and the weight average molecular weight was 8,800. Further, the contact angle of the polymer (11) to water was 107°, and its sliding angle was 9°.

The measurements of the contact angle and the sliding angle were carried out by the following process. That is, a solution having the polymer (11) dissolved in 1,3-bis(trifluoromethyl)benzene, was prepared. The solution was filtrated to obtain a solution containing 4 mass % of the polymer (11) based on the total mass of 1,3(trifluoromethyl)benzene. Then, the solution was applied on a surface of a silicon substrate by carrying out a spin coating method (rotation condition: 2,000 rpm for 30 seconds). Further, by heating the substrate at least to the boiling point of the solvent, the solvent was removed, and a film of the polymer (11) was formed on the surface of the silicon substrate. Then, a droplet of water (2 µL) was placed on the film, and in a state of keeping the substrate in horizontal, the contact angle of the droplet of water to the film, was measured. Further, a droplet of water (50 µL) at 25° C. was placed on the film, and by declining the substrate, the inclination angle of the substrate immediately before the droplet of water fell, was measured. Such value was referred to as a sliding angle. Such measurements were carried out by using a contact angle meter (tradename: DropMaster700, manufactured by Kyowa Interface Science Co., Ltd.).

Example 9

Polymerization Example of Compound (12)

Into a pressure-proof reactor (inner volume: 30 mL), 2.0 g of the compound (12), 10.7 g of R225 and 1.3 g of diisopropylperoxycarbonate which was diluted to 50 mass % by R225, and 0.35 g of isopropyl alcohol, were introduced. Inside of the reactor was frozen and degassed, and then, the inner temperature of the reactor was adjusted to 40° C., and a polymerization reaction was carried out for 18 hours. After the polymerization reaction, the liquid content of the reactor was dropwise added to methanol to recover the formed solid product, and the solid product was vacuum dried at 90° C. for 15 hours. As a result, 1.2 g of a polymer formed by polymerization of the compound (12) (hereinafter referred to as a polymer (12)), was obtained. The polymer (12) was a white solid polymer at 25° C.

As a result of measuring the molecular weight of the polymer (12) in the same manner as in Example 8, the number average molecular weight of the polymer (12) was 4,300, and the weight average molecular weight was 8,800. Further, the contact angle of the polymer (12) to water was 106°, and the sliding angle was 11°.

INDUSTRIAL APPLICABILITY

According to the present invention, a novel fluorocompound having a highly fluorinated norbornane structure, is provided. A polymer obtained by polymerizing the polymerizable compound having the fluorinated norbornane structure, of the present invention, is excellent in water and oil repellency, heat resistance, mold releasability, chemical resistance, transparency, durability and light resistance and low refractive index property, and it is a polymer particularly excellent in dynamic water and oil repellency. The polymer of the present invention is useful as an antifouling agent, a water and oil repellent, a mold lubricant, an optical fiber material, a pellicle material, a lens material, a display surface protection film, etc.

The entire disclosure of Japanese Patent Application No. 2006-190484 filed on Jul. 11, 2006 including specification, claims and summary is incorporated herein by reference in its entirety.

What is claimed is:

1. A compound represented by the following formula (1):

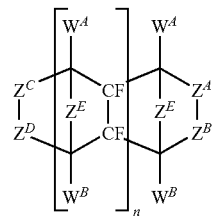

(1)

wherein the symbols in the formula have the following meanings:

$Z^A$, $Z^B$, $Z^C$, $Z^D$, and $Z^E$: each of them is independently —CH(—OC(O)CT=CH$_2$)—, —CF(—CH$_2$OC(O)CT=CH$_2$)— or —CR$^A$R$^B$—, provided that at least one of $Z^A$ to $Z^E$ is —CH(—OC(O)CT=CH$_2$)— or —CF(—CH$_2$OC(O)CT=CH$_2$)—, and at least one of $Z^A$ to $Z^E$ is —CR$^A$R$^B$— (wherein each of R$^A$ and R$^B$ is independently a fluorine atom, a C$_{1-16}$ perfluoroalkyl group or a C$_{1-16}$ perfluoroalkyl group containing an etheric oxygen atom, T is a hydrogen atom, a fluorine atom, a C$_{1-3}$ alkyl group or a C$_{1-3}$ fluoroalkyl group);

$W^A$ and $W^B$: each of them is independently a fluorine atom, a C$_{1-16}$ perfluoroalkyl group or a C$_{1-16}$ perfluoroalkyl group containing an etheric oxygen atom; and n: 0, 1 or 2.

2. A compound represented by the following formula (1A-1):

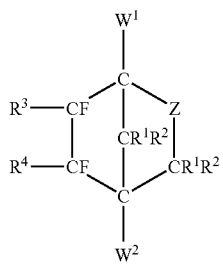

(1A-1)

wherein the symbols in the formula have the following meanings:

Z: —CH(—OC(O)CT$^1$=CH$_2$)— or —CF(—CH$_2$OC(O)CT$^1$=CH$_2$)— (wherein T$^1$ is a hydrogen atom, a fluorine atom, a methyl group or a trifluoromethyl group);

W$^1$ and W$^2$: each of them is independently a fluorine atom or a trifluoromethyl group; and R$^1$, R$^2$, R$^3$ and R$^4$: each of them is independently a fluorine atom or a C$_{1-16}$ perfluoroalkyl group.

3. A compound selected from either one of compounds represented by the following formulae:

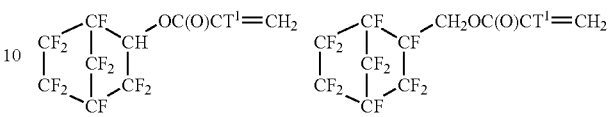

wherein T$^1$ represents a hydrogen atom, a fluorine atom, a methyl group or a trifluoromethyl group.

4. A process for producing a compound represented by the following formula (1), which comprises reacting a compound represented by the following formula (2) with a compound represented by CH$_2$=CTC(O)J:

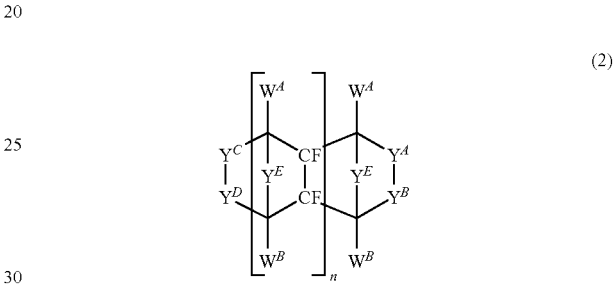

(2)

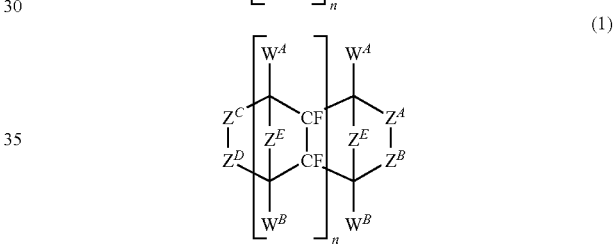

(1)

wherein the symbols in the formulae have the following meanings:

$Y^A$, $Y^B$, $Y^C$, $Y^D$, and $Y^E$: each of them is independently —CH(—OH)—, —CF(CH$_2$OH)— or —CR$^A$R$^B$—, provided that at least one of $Y^A$ to $Y^E$ is —CH(—OH)— or —CF(CH$_2$OH)—, and at least one of $Y^A$ to $Y^E$ is —CR$^A$R$^B$—; and $Z^A$, $Z^B$, $Z^C$, $Z^D$, and $Z^E$: each of them is independently —CH(—OC(O)CT=CH$_2$)—, —CF(—CH$_2$OC(O)CT=CH$_2$)— or —CR$^A$R$^B$—, provided that at least one of $Z^A$ to $Z^E$ is —CH(—OC(O)CT=CH$_2$)— or —CF(—CH$_2$OC(O)CT=CH$_2$)—, and at least one of $Z^A$ to $Z^E$ is —CR$^A$R$^B$—; wherein $Y^A$ corresponds to $Z^A$, $Y^B$ to $Z^B$, $Y^C$ to $Z^C$, $Y^D$ to $Z^D$ and $Y^E$ to $Z^E$, respectively; when each of $Z^A$ to $Z^E$ is —CH(—OC(O)CT=CH$_2$)—, each of $Y^A$ to $Y^E$ is —CH(—OH)—; when each of $Z^A$ to $Z^E$ is —CF(—CH$_2$OC(O)CT=CH$_2$)—, each of $Y^A$ to $Y^E$ is —CF(CH$_2$OH)—; and when each of $Z^A$ to $Z^E$ is —CR$^A$R$^B$—, each of $Y^A$ to $Y^E$ is —CR$^A$R$^B$—; each of R$^A$ and R$^B$ is independently a fluorine atom, a C$_{1-16}$ perfluoroalkyl group or a C$_{1-16}$ perfluoroalkyl group containing an etheric oxygen atom; and T is a hydrogen atom, a fluorine atom, a C$_{1-3}$ alkyl group or a C$_{1-3}$ fluoroalkyl group;

W$^A$ and W$^B$: each of them is independently a fluorine atom, a C$_{1-16}$ perfluoroalkyl group or a C$_{1-16}$ perfluoroalkyl group containing an etheric oxygen atom;

J: a halogen atom; and n: 0, 1 or 2.

5. A compound represented by the following formula (2):

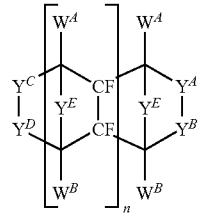
(2)

wherein the symbols in the formula have the following meanings:

$Y^A$, $Y^B$, $Y^C$, $Y^D$, and $Y^E$: each of them is independently —CH(—OH)—, —CF(CH$_2$OH)— or —CR$^A$R$^B$—, provided that at least one of $Y^A$ to $Y^E$ is —CH(—OH)— or —CF(CH$_2$OH)—, and at least one of $Y^A$ to $Y^E$ is —CR$^A$R$^B$— (wherein each of R$^A$ and R$^B$ is independently a fluorine atom, a $C_{1-16}$ perfluoroalkyl group or a $C_{1-16}$ perfluoroalkyl group containing an etheric oxygen atom);

$W^A$ and $W^B$: each of them is independently a fluorine atom, a $C_{1-16}$ perfluoroalkyl group or a $C_{1-16}$ perfluoroalkyl group containing an etheric oxygen atom; and n: 0, 1 or 2.

6. A compound represented by the following formula (2A-1):

(2A-1)

wherein the symbols in the formula have the following meanings:

Y: —CH(—OH)— or —CF(—CH$_2$OH)—;

R$^1$, R$^2$, R$^3$ and R$^4$: each of them is independently a fluorine atom or a $C_{1-16}$ perfluoroalkyl group; and W$^1$ and W$^2$: each of them is independently a fluorine atom or a trifluoromethyl group.

7. A compound selected from compounds represented by the following formulae:

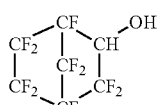 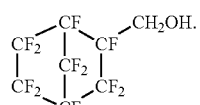

8. A process for producing a compound represented by the following formula (2), which comprises subjecting a compound represented by the following formula (3) to a reduction reaction:

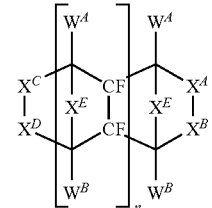
(3)

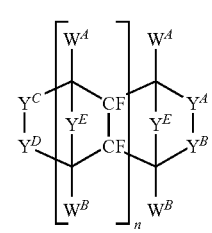
(2)

wherein the symbols in the formulae have the following meanings:

$X^A$, $X^B$, $X^C$, $X^D$ and $X^E$: each of them is independently —C(O)—, —CF(C(O)G)- or —CR$^A$R$^B$—, provided that at least one of $X^A$ to $X^E$ is —C(O)— or —CF(—C(O)G)-, and at least one of $X^A$ to $X^E$ is —CR$^A$R$^B$—;

$Y^A$, $Y^B$, $Y^C$, $Y^D$, and $Y^E$: each of them is independently —CH(—OH)—, —CF(CH$_2$OH)— or —CR$^A$R$^B$—, provided that at least one of $Y^A$ to $Y^E$ is —CH(—OH)— or —CF(CH$_2$OH)—, and at least one of $Y^A$ to $Y^E$ is —CR$^A$R$^B$—; wherein $X^A$ corresponds to $Y^A$, $X^B$ to $Y^B$, $X^C$ to $Y^C$, $X^D$ to $Y^D$ and $X^E$ to $Y^E$, respectively; when each of $Y^A$ to $Y^E$ is —CH(—OH)—, each of $X^A$ to $X^D$ is —C(O)—; when each of $Y^A$ to $Y^E$ is —CF(—CH$_2$OH)—, each of $X^A$ to $X^D$ is —CF(—C(O)G)-; and when each of $Y^A$ to $Y^E$ is —CR$^A$R$^B$—, each of $X^A$ to $X^D$ is —CR$^A$R$^B$—; each of R$^A$ and R$^B$ is independently a fluorine atom, a $C_{1-16}$ perfluoroalkyl group or a $C_{1-16}$ perfluoroalkyl group containing an etheric oxygen atom; G is a halogen atom or a $C_{1-10}$ alkoxy group;

$W^A$ and $W^B$: each of them is independently a fluorine atom, a $C_{1-16}$ perfluoroalkyl group or a $C_{1-16}$ perfluoroalkyl group containing an etheric oxygen atom; and n: 0, 1 or 2.

* * * * *